US00PP16090P3

(12) United States Plant Patent
van der Voort

(10) Patent No.: US PP16,090 P3
(45) Date of Patent: Nov. 1, 2005

(54) LILY PLANT NAMED 'TARRAGONA'

(50) Latin Name: *Lilium L. orienpet (oriental×trumpet)*
Varietal Denomination: Tarragona

(75) Inventor: Cees A. van der Voort, Katwijk (NL)

(73) Assignee: Vletter & Den Haan Beheer B.V., Katwijk (NL)

( * ) Notice: Subject to any disclaimer, the term of this patent is extended or adjusted under 35 U.S.C. 154(b) by 0 days.

(21) Appl. No.: 10/607,264

(22) Filed: Jun. 27, 2003

(65) Prior Publication Data

US 2004/0172732 P1 Sep. 2, 2004

Related U.S. Application Data

(60) Provisional application No. 60/392,040, filed on Jun. 28, 2002.

(51) Int. Cl.[7] ..... A01H 5/00

(52) U.S. Cl. ..... Plt./313

(58) Field of Search ..... Plt./315

(56) References Cited

FOREIGN PATENT DOCUMENTS

| | | |
|---|---|---|
| EP | 9394 | 5/2002 |
| PL | 0 1904 | 2/2004 |
| ZA | 20032852 | 3/2003 |

OTHER PUBLICATIONS

UPOV 'hit' on 'Tarragona', GTI Jouve retrieval software, Plant Variety Database, Feb. 2004.*

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Tarragona' characterized by its creamy white flowers with yellow center color and contrasting orange pollen, and vigorous growth.

1 Drawing Sheet

Latin name of the genus and species of the plant claimed: *Lilium L. orienpet* (*oriental×trumpet*).
Variety denomination: Tarragona.

BACKGROUND OF THE INVENTION

The present invention comprises a new and distinct cultivar of lily plant, botanically known as *Lilium L. orienpet* (*oriental×trumpet*), and hereinafter referred to by the cultivar name 'Tarragona'.

'Tarragona' is a product of a planned breeding program which had the objective of creating new lily cultivars having many large, upright flowers and vigorous growth habit.

'Tarragona' originated from a hybridization made by the inventor, Cees A. van der Voort, in a controlled breeding program in Rijnsburg, the Netherlands in October, 1997. Both the female and male parents are unnamed proprietary *Lilium L.* seedlings.

'Tarragona' was discovered and selected as one flowering plant within the progeny of the stated cross by the inventor in October, 1997 in a controlled environment in Rijnsburg, the Netherlands.

The first act of asexual reproduction of 'Tarragona' was accomplished when scales were taken from the initial selection and grown to maturity in a controlled environment in Rijnsburg, the Netherlands by, or under the supervision of, Cees A. van der Voort. Horticultural examination of selected plants has demonstrated that the combination of characteristics as herein disclosed for 'Tarragona' are firmly fixed and are retained through successive generations of asexual reproduction.

BRIEF DESCRIPTION OF THE INVENTION

The following traits have been repeatedly observed and are determined to be basic characteristics of 'Tarragona' which in combination distinguish this lily as a new and distinct cultivar:

1. large, creamy white flowers with yellow center color and contrasting orange pollen; and
2. vigorous growth habit.

Of the many commercial cultivars known to the present inventor, the most similar in comparison to 'Tarragona' is the Lily cultivar 'Conca D'or', described in pending U.S. plant patent application Ser. No. 09/357,100. However, in side-by-side comparisons conducted by the inventor in Stige, Denmark, the main distinction between the two cultivars is:

1. Both plants of 'Tarragona' and 'Conca D'or' have the same stem firmness, but the 'Tarragona' is significantly shorter in plant height than 'Conca D'or'.

'Tarragona' has not been observed under all possible environmental conditions. The phenotype of the new cultivar may vary significantly with variations in environment such as temperature, light intensity, and daylength without any change in genotype.

BRIEF DESCRIPTION OF THE DRAWING

The accompanying color photographic drawing shows a side-view of a typical plant of 'Tarragona', with colors being as true as possible with illustrations of this type.

The photographic drawing shows the large, creamy white flowers with yellow center color and contrasting orange pollen, and buds and leaves of 'Tarragona'.

DETAILED BOTANICAL DESCRIPTION

The following observations, measurements and values describe the new cultivar as grown in Rijnsburg, The Netherlands under conditions which closely approximate those generally used in commercial practice. The plant is grown under controlled climate conditions, preferably in greenhouse constructions. Color references are made to The Royal Horticultural Society (R.H.S.) Colour Chart (publication date 2001), except where general colors of ordinary significance are used. Color values were taken under daylight conditions at approximately 12:00 p.m. in Rijnsburg, The Netherlands. The age of the plant described is about 90 days.

Parentage:

*Male parent.*—Unnamed proprietary seedling (unpatented).

*Female parent.*—Unnamed proprietary seedling (unpatented).

Propagation: Scales were taken from the bulbs.

Plant:

*General appearance and form.*—Height: Medium to tall, 100 cm, depending on growing conditions.

*Flowering season.*—All year round in controlled climate conditions in a greenhouse.

*Winter hardiness/weather tolerance.*—None.

*Lastingness of the individual bloom.*—Minimum 21 days, depending on storing conditions.

*Rooting habit.*—Vigorous.

*Fragrance.*—Very weak.

Stem description:

*Length.*—Medium to long, 95 cm, depending on growing conditions.

*Diameter.*—3 mm.

*Strength.*—Strong.

Foliage:

*Overall shape of leaf.*—Ovate.

*Quantity.*—Approximately 50–60, depending on growing conditions.

*Length.*—Medium to long, 11 cm, depending on growing conditions.

*Width.*—Medium, 2.5 cm, depending on growing conditions.

*Texture.*—Minimal pubescence.

*Color of upper surface.*—Mature leaf: Medium green — RHS 137A. Immature leaf: Medium green — RHS between 137C and 137D.

*Color of lower surface.*—Mature leaf: Medium green — RHS 137C. Immature leaf: Medium green — RHS 137B.

*Venation color.*—Upper surface: Medium green — RHS 137A (mature leaf); medium green — RHS between 137C and 137D (mature leaf). Lower surface: Medium green (mature and immature leaf) — RHS 138B.

*Petiole color.*—Medium green — RHS 138B.

Flowers:

*Flower type and habit.*—Raceme.

*Flower size.*—13 cm diameter.

*Overall shape.*—Hexagonal star in form and trumpet-shaped in cross-section.

*Average number of flowers per lateral branch.*—4, depending on growing conditions.

*Tepals.*—Number of tepals: 6. Texture: Papillose. Tepal size: Short to medium length, 6 cm; medium width, 4 cm. Tepal Color: Upper surface: Yellow RHS 13B and RHS 4D at the edges. Lower surface: Yellow RHS 13B and RHS 4D at the edges.

Bud:

*Form.*—Tapering.

*Color.*—Light yellow — RHS 4D.

*Length.*—7 cm, depending on growing conditions.

*Diameter.*—3 cm depending on growing conditions.

*Peduncles.*—6.5 cm length, angle horizontal, color: medium green — RHS 138B.

Reproductive organs:

*Stamen.*—Number: 6. Color: Yellowish green RHS 149C.

*Seeds.*—None.

*Fruit.*—None.

*Anthers.*—Number: 6. Color: Yellow-Green — RHS 149A.

*Pollen.*—Color: Greyed purple RHS 187C.

*Stigma.*—Number: 1. Color: Greyed-purple — RHS 187A.

Pest/disease resistance/susceptibility: No known information.

I claim:

1. A new and distinct cultivar of lily plant named 'Tarragona', as illustrated and described herein.

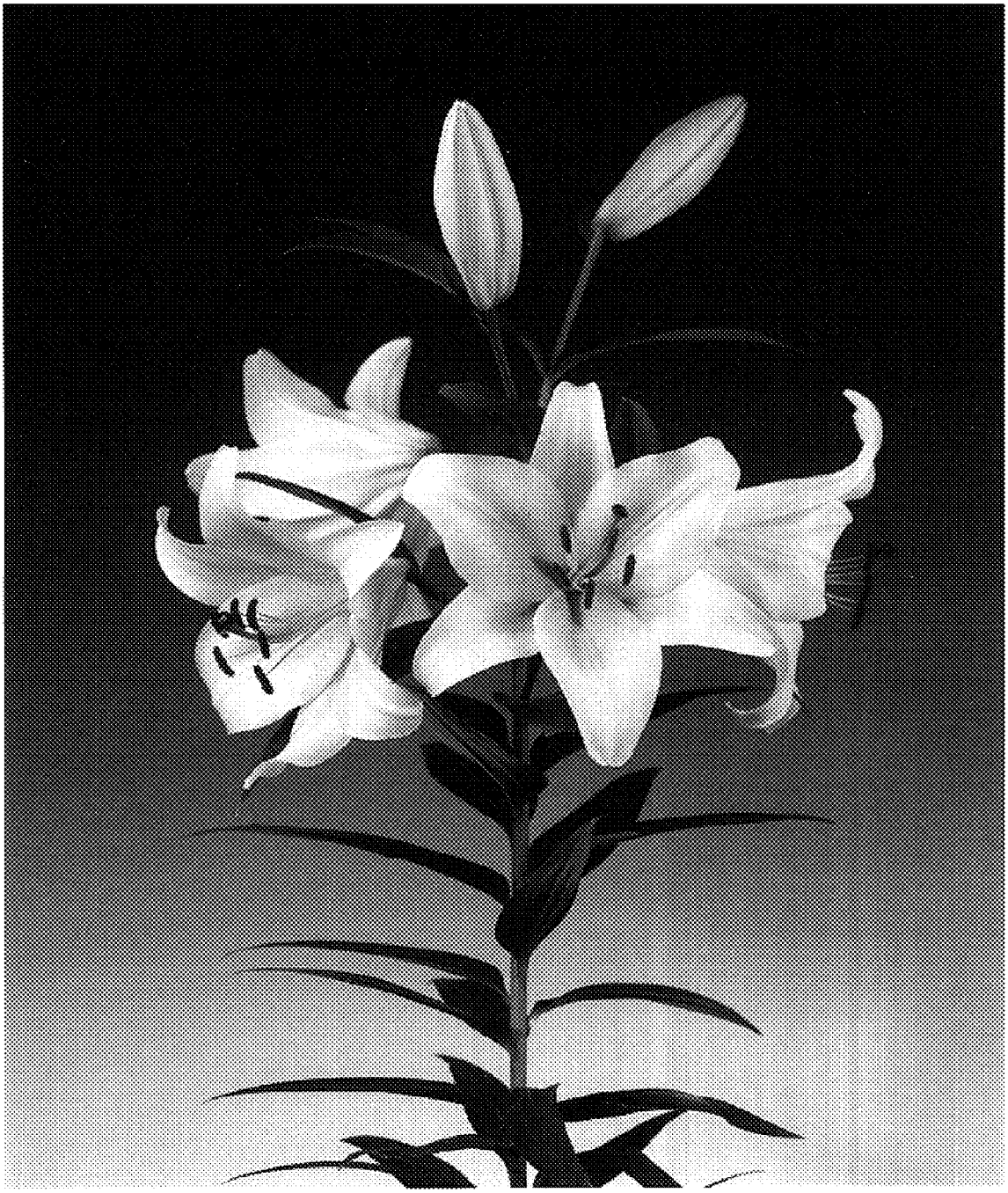

* * * * *